(12) United States Patent
Coszach et al.

(10) Patent No.: US 8,471,062 B2
(45) Date of Patent: Jun. 25, 2013

(54) METHOD OF PURIFYING LACTIC ACID BY CRYSTALLIZATION

(75) Inventors: Philippe Coszach, Courcelles (BE); Jean-Christophe Bogaert, Ligne (BE); Pierre-Antoine Mariage, Pipaix (BE); Angelo Chianese, Rome (IT); Maria-Paola Parisi, Rome (IT)

(73) Assignee: Galactic S.A., Escanaffles (BE)

( * ) Notice: Subject to any disclaimer, the term of this patent is extended or adjusted under 35 U.S.C. 154(b) by 0 days.

(21) Appl. No.: 13/141,920

(22) PCT Filed: Nov. 18, 2009

(86) PCT No.: PCT/EP2009/065385
§ 371 (c)(1), (2), (4) Date: Sep. 13, 2011

(87) PCT Pub. No.: WO2010/072473
PCT Pub. Date: Jul. 1, 2010

(65) Prior Publication Data
US 2011/0319660 A1    Dec. 29, 2011

(30) Foreign Application Priority Data

Dec. 24, 2008 (BE) .................. 2008/0702

(51) Int. Cl.
*C07C 51/64* (2006.01)

(52) U.S. Cl.
USPC ......................................... 562/580; 562/589

(58) Field of Classification Search
CPC combination set(s) only.
See application file for complete search history.

(56) References Cited

U.S. PATENT DOCUMENTS

| 5,681,728 A | 10/1997 | Miao |
| 6,489,508 B1 | 12/2002 | Van Gansbeghe et al. |
| 6,630,603 B1 * | 10/2003 | Van Breugel et al. ........ 562/580 |
| 7,244,596 B2 | 7/2007 | Baets et al. |

FOREIGN PATENT DOCUMENTS

| EP | 1 953 234 | 8/2008 |
| WO | WO 00/56693 A1 | 9/2000 |
| WO | WO 02/22544 A1 | 3/2002 |
| WO | WO 02/22545 A1 | 3/2002 |
| WO | WO 2010/072473 A1 | 7/2010 |

OTHER PUBLICATIONS

International Search Report for PCT/EP2009/065385, dated Jan. 21, 2010, 3 pages.
H. Borsook, et al., "The Preparation of Crystalline Lactic Acid," *J. Biol. Chem*, 449-460, (1933).
L. B. Lockwood, et al., "Section 1. Chemistry and Enzymology of Lactate Isomers, Lactic Acid," *N. Y. Acad. Sci.* 119, 854-867 (1965).
Holten, C.H.., "Lactic acid: Properties and chemistry of lactic acid and derivatives", 20-22, *Verlag Chemie*, (1971).
H. A. Andreetta, et al., "Absolute calibration method for exclusion liquid chromatography (GPC), Theoretical basis and methodology," *Makromol. Chem., Rapid Commun*, 6, 419-423, (1985).

* cited by examiner

*Primary Examiner* — Paul A Zucker
(74) *Attorney, Agent, or Firm* — Reichel IP LLP; Kevin R. Erdman; Mark C. Reichel

(57) ABSTRACT

Method for purifying lactic acid by crystallization in one or a plurality of steps, characterized in that crystals are formed from an impure aqueous lactic acid solution having a color of >500 Hazen, at a concentration between 85 and 95% by controlling the lactic acid oligomer content expressed in terms of a relative monomer content greater than 80% and controlling the degree of supersaturation of the solution between 1 and 60% in order to obtain lactic acid crystals having a specific surface area by mass of <0.05 $m^2/g$.

7 Claims, 2 Drawing Sheets

METHOD OF PURIFYING LACTIC ACID BY CRYSTALLIZATION

CROSS-REFERENCE TO RELATED APPLICATION

This application is a National Stage filing, under 35 U.S.C. §371, of International Application Serial No. PCT/EP2009/065385, filed Nov. 18, 2009 and designating the United States, which claims priority to Belgium Application Serial No. 2008/0702, filed Dec. 24, 2008, the entire disclosures of which are expressly incorporated herein by reference.

FIELD OF THE INVENTION

The present invention relates to a method for purifying lactic acid in order to produce, in a single crystallisation step, lactic acid crystals having a specific surface area by mass of <0.05 $m^2/g$.

BACKGROUND OF THE INVENTION

It is well known that lactic acid or hydroxy-2-propanoic acid which is an α-hydroxy carboxylic acid can be produced by fermentation. Further processes for obtaining lactic acid are known to those skilled in the art, via chemical conversions of petrochemical reagents such as the hydrolysis of lactonitrile obtained from acetaldehyde, chlorination and hydrolysis of propionic acid or via propene nitration.

It is also known that lactic acid is found in two diastereoisomeric forms, the L(+) form and the D(−) form, and encounters novel applications every day, from the conventional use as a food preservative to novel developments such as the synthesis of solvents, pesticides, herbicides, biodegradable polymers, etc.

However, due to the increasing stringency of the required quality criteria and the need to achieve production costs compatible with the commodities market, it is vital to be able to reduce energy costs while maintaining a quality level meeting the strictest requirements. Moreover, controlling, or reducing, the energy consumption of industrial processes is of particular interest in the current context of environmental pressure and the restriction of fossil energy resources.

It is also known that the purity of a lactic acid is, among other things, evaluated by measuring the colour at ambient temperature (APHA scale in Hazen units) and by a thermal stability test consisting of measuring the colour (APHA scale in Hazen units) of the substance after heating at reflux at a temperature of 200 degrees Celsius (° C.) for two hours. A lactic acid solution is generally considered to be heat-stable if the colour after cooling to ambient temperature does not exceed 50 Hazen.

However, for some specific applications such as for example for the production of polylactic acid, lactic acid should have a very high purity and a very low thermal stability index, generally less than 50 Hazen, or in some cases less than 30 Hazen. It consists of a "polymer" grade if it enables the production of a polylactic acid having a molecular weight greater than 100,000 Dalton as specified in the patent (EP 1953 234 A1).

Furthermore, the prior art describes in detail that the industrial purification of a heat-stable grade lactic acid from a fermentation juice rich in lactic acid can be carried out using various technologies generally including common steps:

Clarifying the fermentation must: (centrifugation, flocculation/filtration, microfiltration, etc.)

Removing the ions (electrodialysis, ion exchange resins, liquid/liquid extraction, etc.)

Removing the colour and other impurities (membrane filtration, activated carbon, etc.)

Concentrating/distilling the lactic acid: these steps should be combined to obtain a high yield.

These purification methods are described for example in the patents (U.S. Pat. Nos. 6,489,508; 5,681,728; 7,244,596). Using these techniques for purifying a lactic acid having a concentration greater than 85%, a specific colour greater than 500 Hazen and derived from fermentation, at the present time, it is necessary to use at least one distillation step to produce a heat-stable grade lactic acid.

The disadvantage of these types of methods is the amount of energy required and the complex equipment required.

It is also known that lactic acid in concentrated solution can be crystallised (H. Borsook, H. M. Huffman, Y-P. Liu, J. Biol. Chem. 102, 449-460 (1933), L. B. Lockwood, D. E. Yoder, M. Zienty, Ann N.Y. Acad. Sci. 119, 854 (1965), Holten C. H., "Lactic acid: Properties and chemistry of lactic acid and derivatives", 20-22, Verlag Chemie, 1971).

The methods according to the prior art describing the production of lactic acid crystals in a crystallisation stage do not enable the production of heat-stable grade lactic acid crystals unless either a lactic acid of relatively high quality (colour <500 Hazen) is used as the initial lactic acid, or organic solvents are used. All these constraints will have a non-negligible impact on production costs. Furthermore, none of these methods mentions the size of the crystals obtained.

In the patent WO 0222545, a method for purifying lactic acid is also described, but including, before the crystallisation step, an extraction step in organic solvent, instead of distillation. It is known to those skilled in the art that a small percentage of organic extractant is found in the aqueous phase from this extraction, requiring an additional purification step to remove this solvent residue.

However, in some cases, the impure fermentation juice may be purified without using organic solvent.

The crystallisation of lactic acid is also described in the patent WO 0056693, but requires starting with a much purer aqueous lactic acid solution (the colour of the lactic acid solution not exceeding 83 Hazen).

The literature also contains methods for purifying lactic acid, particularly as described in the patent WO 0222544, including one or a plurality of crystallisation steps associated with a distillation step.

The purity of crystals is generally associated with the specific surface area by mass thereof.

The specific surface area by mass (SSM) of crystals is the area developed by the crystals per unit of weight. The specific surface area by mass (SSM) is used to compare the dimensional characteristics of crystals of a suspension or a powder with those of another suspension or powder. This specific surface area can be measured by means of optical imaging on the basis of a volume (Vm) and the mean surface area (Sm) of hundreds of crystals (by measuring the length of the face thereof) and the density of the crystals (Dc):

$$SSM=Sm/(Vm*Dc).$$

Indeed, after the liquid/solid separation following crystallisation, the quantity of residual parent solution per unit of mass of crystals is proportional to the surface area thereof. The impurities being essentially found in the parent solution, the smaller the surface area developed by the crystals per unit of mass and the lower impurity content of the mass of crystals. For example, this is the case of beet and cane sugar.

It is also known that liquid/solid separation is also facilitated with large crystals.

There is a need for a method for producing, by crystallisation, heat-stable grade lactic acid at least cost from an impure aqueous solution having a colour greater than 500 Hazen working at low temperatures, preferably not exceeding 30° C. and more preferentially between 4 and 26° C.

During crystallisation, said step may particularly be influenced by two factors, nucleation and supersaturation.

There are two types of nucleation, primary nucleation and secondary nucleation.

In the case of primary nucleation, micro-organisms appear in a medium not yet containing any crystals from the precipitating phase. If the micro-organisms are formed in the volume of the solution, the nucleation is referred to as primary homogeneous. If, on the other hand, they are formed on the walls of the crystallisers, on the stirrers or on solid particles floating in the solution, the nucleation is referred to as primary heterogeneous.

In the case of secondary nucleation, micro-organisms appear in a medium wherein crystals from the precipitating phase already exist. If the solution contains crystals, they may collide with each other, hit the walls, the stirrer, other solid particles and thus release microscopic particles. These particles can then grow. Secondary nucleation may also occur following a sudden rise in supersaturation.

The nucleation temperature (Tn) mentioned in the present patent application consists of the secondary nucleation temperature.

In the metastability zone, the supersaturation (S) in gallons per liter (g/l) at a given temperature can be defined as the difference between the concentration in the solution (C) (g/l) and the concentration at saturation (C*) (g/l): S=C−C*.

The degree of supersaturation ($Ds^c$) of a solution at a given concentration "c" is: $Ds^c=(Ts^c-T)/(Ts^c-Tn^c)$.

Where $Ts^c$ is the solubilisation temperature, T is the operating temperature, and $Tn^c$ is the secondary nucleation temperature.

The very structure of lactic acid bearing both a hydroxyl function and a carboxylic acid group gives rise to condensation reactions generating lactoyllactic, dilactoyllactic, trilactoyllactic, . . . (n-lactoyllactic) units also referred to as lactic acid oligomers. These condensation or oligomerisation reactions tends towards equilibrium but are all the more likely if the starting aqueous solution concentration and temperature are high (Holten C. H., "Lactic acid: Properties and chemistry of lactic acid and derivatives", Verlag Chemie, 1971).

The monomer content in relation to the total lactic acid concentration (monomer and oligomer) can be estimated using the following equation provided that the total acidity is less than 105%:

Relative monomer content=(TA%−(TA %−FA%)*2)/ TA %, where: TA=total acidity determined by acid-base titration after saponification and expressed as lactic acid monomer; and FA=free acidity determined by direct acid-base titration and expressed as lactic acid monomer.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein.

Corresponding reference characters indicate corresponding parts throughout the several views. The exemplifications set out herein illustrate exemplary embodiments of the disclosure and such exemplifications are not to be construed as limiting the scope of the disclosure in any manner.

BRIEF SUMMARY OF THE INVENTION

Figure 1:
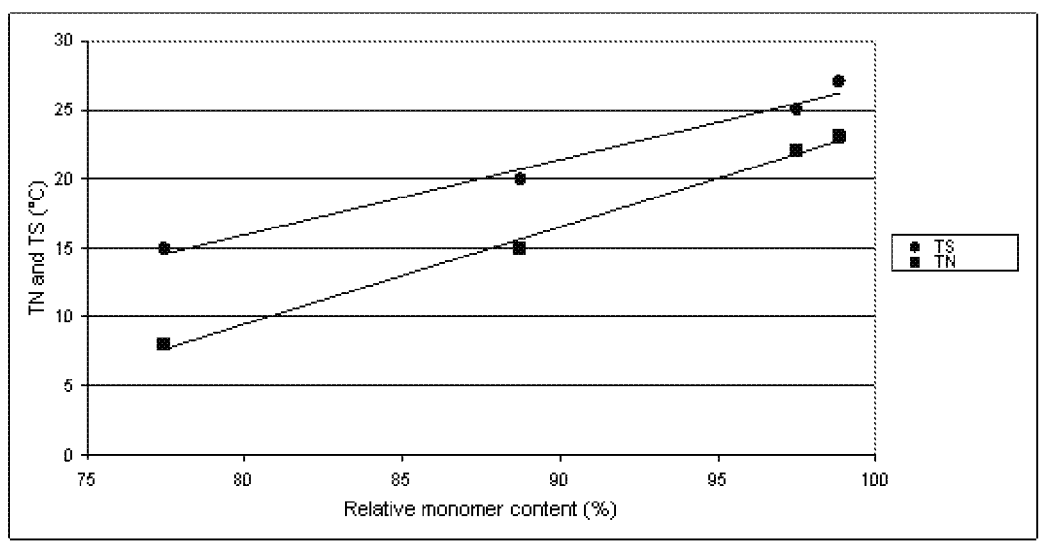
FIG. 1 is a graph showing the progression of nucleation temperature (Tn) solubilaztion temperature (Ts) according to the relative monomer content of a lactic acid having a total acidity (TA) of 89%.

The present invention relates to a method for purifying lactic acid in order to produce crystals having a specific surface area by mass less than 0.05 m²/g from an impure aqueous solution having a colour greater than 500 Hazen.

The present invention also relates to a method for purifying lactic acid by crystallisation and preferably without distillation, in order to produce crystals having a surface area by mass <0.05 m²/g wherein the content of other impurities is such that a 90% aqueous solution prepared from crystals is of heat-stable grade and preferably having a colour less than 30 Hazen after heating to 200° C. for 2 hours.

The present invention also relates to a method for purifying lactic acid by crystallisation performed by controlling the oligomer content of the solution and also by controlling the supersaturation factor.

DETAILED DESCRIPTION OF THE INVENTION

The applicant has developed a method for purifying lactic acid including a step for forming crystals having a specific surface area by mass less than 0.05 m²/g of crystals from a lactic acid solution having a colour greater than 500 Hazen and having a relative monomer content greater than 80% characterised in that:
1) The solution is cooled at a low degree of supersaturation;
2) The solution is seeded with lactic acid crystals;
3) The crystals are grown at low supersaturation; and
4) The crystals are retrieved by separating same from the liquid phase.

It was also discovered that crystallisation needed to be carried by controlling the temperature in order to retain a degree of supersaturation less than 60% and preferably between 1 and 40%.

Unexpectedly, the applicant discovered that residual impurities not eliminated after crystallisation were mainly present in the surface impregnation liquid and that the specific surface area of the crystals was closely linked with the supersaturation value. Indeed, at low supersaturation, the crystals have a low surface density whereas, at high supersaturation, the applicant observed a significant elongation of lactic acid crystals (needle shape) giving rise to a markedly greater crystalline surface area.

The applicant also unexpectedly discovered that, by controlling the relative monomer content of the solution, i.e. by keeping same above 80% and preferably above 90%, it was possible to affect crystallisation significantly by increasing the solubility temperature and the nucleation temperature and thus the crystallisation yield. Indeed, it was discovered that a reduction in the relative monomer content has a significant influence on the solubility and nucleation temperatures of lactic acid.

Various purified lactic acids, each having different free acidities for the same total acidity (89%), were tested by introducing same into a 5 liter (L) finely thermostatically controlled reactor equipped with a helical stirring blade.

In order to measure the solubility point precisely, the temperature is adjusted to 5° C. below the theoretical solubility temperature. In our case, the temperature in the reactor is adjusted to 25° C. (theoretical solubility temperature of 30° C. for the selected concentration and an oligomer-free product). The temperature is then progressively increased until no further crystals are present. The temperature at which the final crystal disappears is the experimental solubility temperature.

We measured the secondary nucleation temperature for more reproducibility. For this purpose, a few large crystals (three or four) are introduced into the slightly subcooled solution (26° C.). These crystals are used to initiate nucleation.

To obtain nucleation, the solution is cooled according to a cooling gradient of 10° C./hr.

The nucleation temperature is measured when the first crystal (excluding crystals in solution) appears.

FIG. 1 gives the progression of Tn and Ts according to the relative monomer content of a lactic acid having a TA of 89%.

It is clear in Table 1 and FIG. 1 that reducing the relative monomer content has a significant influence on the solubility and nucleation temperatures of lactic acid.

TABLE 1

| Total acidity (%) | Free acidity (%) | Relative monomer content (%) | Tn ° C. | Ts ° C. |
|---|---|---|---|---|
| 89 | 88.2 | 99 | 23 | 27 |
| 89 | 87.6 | 97.5 | 22 | 25 |
| 89 | 84 | 89 | 15 | 20 |
| 89 | 78.7 | 77 | 8 | 15 |

Figure 2:
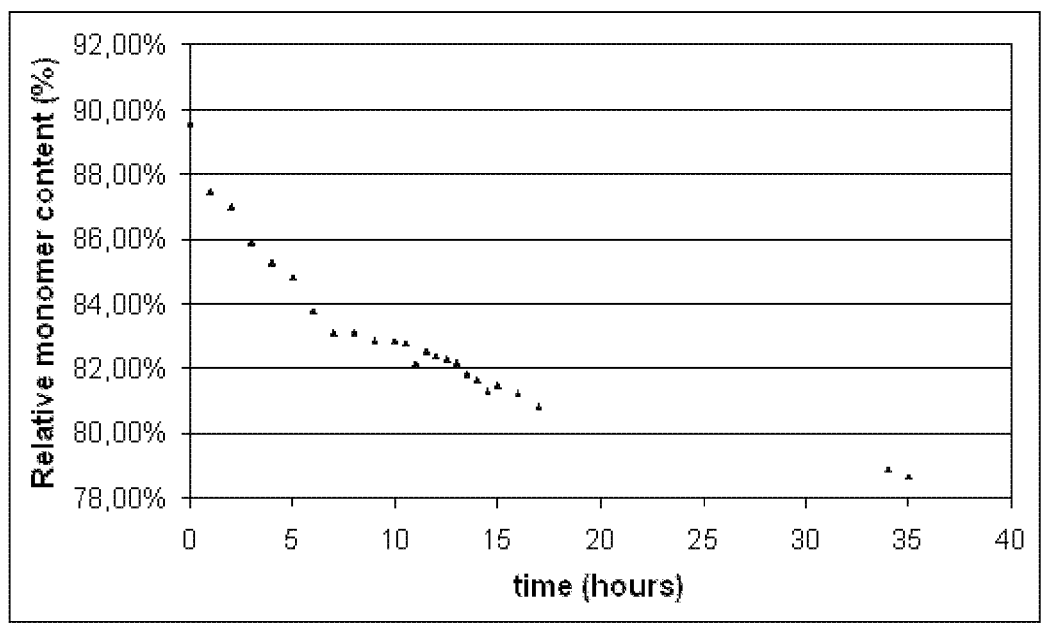
FIG. 2 is a diagram showing the variation in a monomeric lactic acid content of an impure lactic acid solution having a total acidity of 93% and a colour index of 2850 Hazen, and kept under stirring at 40° C.

It was also discovered that the kinetics of these oligomerisation reactions are sufficiently rapid to influence crystallisation purification methods, as demonstrated by the diagram in FIG. 2 representing the variation in the monomeric lactic acid content of an impure lactic acid solution, having a total acidity of 93% and a colour index of 2850 Hazen, and kept under stirring at 40° C.

The applicant unexpectedly discovered that it was preferable to use a starting lactic acid solution having a total acidity between 85 and 95% and preferably having a total acidity between 88 and 93% and having a relative monomer content greater than 80% and preferably between 90 and 100% in order to obtain, after purification, according to the method according to the invention, crystals having the desired properties.

The lactic acid solution having a colour greater than 500 Hazen is preferentially obtained from a fermentation juice pre-purified, for example, by conventional and/or membrane filtration, by running on ion exchange resins and/or on activated carbons, and concentrated using techniques known to those skilled in the art for the intended purpose but may also be obtained from any other source of lactic acid such as, non-exhaustively, lactic acid production waste or polylactic acid recycling after hydrolysis.

The crystallisation per se and outside the control applied to the oligomerisation and supersaturation can be carried out using any crystallisation technology known to those skilled such as those described in Techniques de l'Ingénieur "Cristallisation Industrielle: Aspects Pratiques J 2 788) such as for example scraped surface crystallisers, stirred crystallisers, adiabatic evaporation crystallisers, classifying crystallisers (such as DTP Swenson, DP Tsukishima and Turbulence Messo), fluidised bed crystallisers (such as Oslo or Krystal), forced circulation crystallisers, direct contact cooling crystallisers, multiple effect multi-stage crystallisers. Given that the lactic acid concentration needs to be greater than 75%, this step can also be carried out with crystallisation technologies using a molten medium (such as the brands Kobe Steel, Proabd, Sulzer, Phillips, Brodie, 4C Tsukishima, TNO, Brenband, Niro).

Crystal-parent solution separation can be carried out using any techniques known to those skilled in the art as described for example in Perry's Chemical Engineers' Handbook, chapter 8 (settling, filtration, centrifugation, drying, washing column).

The parent solution retrieved following liquid/solid separation can be recycled downstream from crystallisation to ensure a higher overall yield.

The crystals can also be washed and, in this case, the crystals will be washed using a lactate, lactic acid or water solution either by washing the crystal cake during the solid-liquid separation step or by resuspending the crystals followed by crystal-washing solution separation.

To avoid losing too much lactic acid due to solubilisation during washing, the washing solution will preferentially be a saturated or slightly unsaturated lactic acid solution in order to induce light "wiping" of the crystals during washing. In the latter case, washing will preferentially be carried out by controlling the temperature so as to control "the wiping" while preventing an excessive loss of crystal mass.

The lactic acid crystals can be redissolved in water. The lactic acid solution can be discoloured and purified for example on activated carbon or using any techniques known to those skilled in the art for purifying or discolouring lactic acid (membrane, ion exchange resins, adsorbent resins, electrochemical treatment (reduction, oxidation), etc.

The filtrate retrieved following liquid/solid separation can be recycled downstream from crystallisation to ensure a higher overall yield.

EXAMPLES

Further details and specificities of the invention, given hereinafter as non-limitative examples, emerge from the description as some possible embodiments thereof.

Example 1

Influence of Supersaturation on Crystal Size

One kilogram of lactic acid from a fermentation juice, which is filtered, pre-purified on ion exchange resins and activated carbon, concentrated to 99% and having a colour of 2000 Hazen, a relative monomer content of 96% and diluted to a lactic acid concentration of 92% is introduced into a 5 L finely thermostatically controlled reactor equipped with a helical stirring blade.

The solubility and secondary nucleation temperatures measured according to the protocol described in the prior art are 26° C. and 18° C., respectively.

Two tests are then carried out: 1) a crystallisation test at low supersaturation (Ts−1° C.)($Ds^c$=12.5%); and 2) a crystallisation test at high supersaturation (Tn+1° C. or Ts−7° C.) ($Ds^c$=87.5%).

The temperature of the solution is set according to the degree of supersaturation and the solution is seeded with 20 grams (g) of lactic acid crystals.

The solutions are cooled progressively according to a cooling gradient of 3° C./hr in order to prevent nucleation even at high supersaturation for 5 hours. The temperatures are then 10 and 4° C. respectively and maintained for 19 hours to allow the crystals to grow.

The crystal size measurements were made using an optical microscope (Askania RME5) equipped with a digital camera (Nikon Coolpix 4500) with crystal measurement software supplied by Leica. For both test conditions, the length (L1) and thickness (L2) of 200 crystals were measured.

In Table 2, it can be observed that the morphology of the crystals obtained at low supersaturation ($Ds^c$=12.5%) has a length over width ratio of 4, whereas, at high supersaturation ($Ds^c$=87.5%), they are in the form of needles with a length over width ratio of 7.4.

The specific surface area by mass of the crystals obtained at low supersaturation is 0.03 m²/g whereas that of the crystals at high supersaturation is 0.06 m²/g. This is calculated by taking the surface area and the volume of a parallelepiped having a length L1 and width and thickness L2. The density of lactic acid in crystal form is estimated at 1.22 g/ml.

TABLE 2

| Supersaturation | Length L1 (μm) | | Thickness L2 (μm) | | Length/width ratio | | Specific surface area by mass |
|---|---|---|---|---|---|---|---|
| $Ds^c$ | Mean size | st. dev. | Mean size | st. dev. | average | st. dev. | m²/g |
| 12.5% | 388.1 | 179.2 | 104.3 | 50.3 | 4.0 | 1.4 | 0.03 |
| 87.5% | 411.5 | 164.7 | 60.2 | 21.2 | 7.4 | 3.4 | 0.06 |

TABLE 3

| | Ts ° C. | Tn ° C. |
|---|---|---|
| 90% | 25 | 18 |

The solution is separated into 3 parts of 1 kg and cooled, one to Ts−1° C. (24° C.) ($Ds^c$=14%), the second to Ts−3.5° C. (21.5° C.) ($Ds^c$=50%) and the final part to Tn+1° C. (19° C.) ($Ds^c$=86%). All three are introduced into 5 L finely thermostatically controlled reactors equipped with a helical stirring blade and seeded with lactic acid crystals at a rate of 40 g/kg.

The solutions are cooled progressively according to a cooling gradient of 3° C./hr in order to prevent nucleation even at high supersaturation for 5 hours. The temperatures are then 9 and 4° C. respectively and maintained for 19 hours to allow the crystals to grow.

The crystals are then dried on a Rousselet Robatel RC 30 Vx R centrifuge at 1500 rpm thermostatically controlled via a double shell at 15° C. and then washed with a 90% purified lactic acid solution also at 15° C. at a rate of 25 g of washing fluid per 100 g of crystals. The quantities and the lactic acid content of the crystals retrieved in this step are specified in table 4. The lactic acid content is determined by means of enzyme analysis using a kit manufactured by SCIL (reference enzytec fluid L-lactic acid: Ref 5260).

TABLE 4

| Supersaturation % | Lactic acid content % | Quantity of crystals retrieved after washing/drying g |
|---|---|---|
| 86 | 99.6 | 387 |
| 50 | 99.6 | 351 |
| 14 | 99.6 | 360 |

Example 2

Production of Heat-stable Grade Lactic Acid with a Single Crystallisation 3 kilograms of lactic acid from a fermentation juice, which is filtered, pre-purified on ion exchange resins and activated carbon, concentrated to 99% and having a colour of 1800 Hazen, a relative monomer content of 94% is diluted to a lactic acid concentration of 90%

The solubility and secondary nucleation temperatures (Table 3) of the solution are measured according to the protocol described in the prior art.

At each step, a portion of the crystals are redissolved in a 90% solution in deionised water before analysis.

The 90% lactic acid solution obtained after washing and suspension of the crystals is also placed in contact with 20 g/L of Norit ROX activated carbon overnight at ambient temperature in a sealed cylinder on an orbital stirrer. The solution is filtered and analysed.

The analyses conducted on the 90% crystal solutions are a measurement of the colour at ambient temperature (APHA scale in Hazen units) and a thermal stability test consisting of measuring the colour (APHA scale in Hazen units) of the substance after heating at reflux at a temperature of 200° C. for two hours.

The specific surface area by mass of the crystals is also estimated by measuring the length and thickness of 200 crystals of each sample according to the protocol described in example 1.

The comparison of the results (table 5) indicates that the solution obtained from purified crystals at low supersaturation has a high purity and is heat-stable (<30 Hazen after heating). The purified crystals at moderate supersaturation provide a solution of lower quality but treatment on carbon makes it possible to obtain a heat-stable grade (<50 Hazen after heating). The purified crystals at high supersaturation provide a solution of lower quality, which is not heat-stable, even after treatment on carbon.

Residual acidity: <10 meq/kg
Water content: 40 ppm

A small amount of the purified product obtained above (10 g) is introduced into a test tube with nitrogen scavenging (a plurality of tests was run in parallel). After melting the mixture (100° C.), a tin octoate solution is added in order to comply with a monomer/catalyst molar ratio of 4500. Once the solution has been homogenised, it is immersed in an oil bath wherein the temperature maintained at 180° C.

After one hour, the test tubes are removed from the oil bath, cooled and broken in order to retrieve rigid, opaque polymers. The polymers obtained were analysed by gas chromatography (GC) in chloroform at 35° C. and the mN values between

TABLE 5

| Supersaturation % | Specific surface area by mass $m^2/g$ | Length over thickness ratio | Before crystallisation Colour (fresh solution) (Hazen) | After drying Colour (fresh solution) (Hazen) | Colour after heating (200° C., 2 hrs) (Hazen)) | After washing (25% of a 90% lactic acid solution, 4° C.) Colour (fresh solution) (Hazen) | Colour after heating (200° C., 2 hrs) (Hazen)) | After passage on Noritt ROX activated carbon (20 g/l) Colour (fresh solution) (Hazen) | Colour after heating (200° C., 2 hrs) (Hazen)) | Yield on lactic acid (%) |
|---|---|---|---|---|---|---|---|---|---|---|
| 86 | 0.07 | 8 | 1800 | 235 | 1328 | 120 | 480 | 84 | 297 | 43 |
| 50 | 0.045 | 4.5 | 1800 | 180 | 900 | 63 | 88 | 35 | 45 | 39 |
| 14 | 0.03 | 3 | 1800 | 120 | 500 | 45 | 49 | 22 | 25 | 40 |

Example 3

Production of Polymer Grade Lactic Acid with a Single Crystallisation

A polymerisation test is performed using lactic acid produced in example 2 (lower supersaturation and after treatment on activated carbon) to demonstrate the suitability thereof with the quality requirements required by polylactic acid production.

Lactide Synthesis and Polymerisation Test.

The lactic acid obtained above (~250 g) is introduced into a stirred flask and heated at 160° C. In order to facilitate the rapid extraction of the volatile compound, the unit is placed progressively in a vacuum, the pressure varying between atmospheric pressure and 150 mbar (absolute) for ~10 hours. The lactic acid polymerises to form a pre-polymer characterised by a molecular mass of 1500 Dalton.

The pre-polymer obtained is introduced into a flask heated by a heating cap to 220-250° C. and stirred by a magnetic chip. A polymerisation catalyst, tin octoate, is then introduced into the flask at a rate of 1% by weight in relation to the quantity of pre-polymer introduced.

The flask is topped by a reflux at 180-200° C. followed by a condenser cooled to 80-100° C. and finally a flask for collecting the condensates. The whole is placed in a vacuum between 10 and 20 mbar. The impure lactide collected in the condensate flask is purified twice by recrystallisation in a 1:1 ratio with toluene.

The purified lactide crystals are retrieved by filtration and vacuum-dried in a Rotavapor type apparatus.

The lactide purified in this way has the following features:
L-Lactide: 99.9%
Meso-lactide: 0.1%

90,000 and 110,000 measured (the molecular masses determined on the basis of polystyrene (PS) calibration are corrected on an absolute base using a universal calibration as described by H. A. Andreetta, I. H. Sorokin, R. V. Figini, (1985) Absolute calibration method for exclusion liquid chromatography (GPC). Theoretical basis and methodology Die Makromolekulare Chemie, Rapid Communications, Volume 6, Issue 6, Pages 419-423)) demonstrating the possibility of satisfactory polymerisation of the lactic acid purified according to the proposed method Example 4

Impact of Lactic Acid Concentration on Productivity and Crystal Quality

It was discovered that it was preferable for the lactic acid concentration of the starting solution to be <95% and preferably between 85 and 95%. Indeed, as demonstrated by the example hereinafter, when the starting solution concentration is >95%, there is a dramatic reduction in lactic acid crystal quality and productivity, with all the other parameters remaining within the defined conditions of the method according to the invention.

Into a 5 L finely thermostatically controlled reactor equipped with a helical stirring blade, 2 kilograms of lactic acid from a fermentation juice, which is filtered, pre-purified on ion exchange resins and activated carbon, concentrated to 99% and having a colour of 1900 Hazen, a relative monomer content of 91% and diluted to a lactic concentration of 95.4%.

The solubility and secondary nucleation temperatures (Table 6) of the solution are measured according to the protocol described in the prior art.

TABLE 6

| Lactic acid concentration | Ts ° C. | Tn ° C. |
|---|---|---|
| 95.4% | 42 | 33 |

The solution is cooled rapidly from 46° C. to 41° C. ($Ds^c$=14%) and seeded with 40 g/kg of lactic acid crystals.

The solution is cooled progressively according to a cooling gradient of 3° C./hr in order to prevent nucleation even at high supersaturation for 5 hours. The temperature is then 26° C. Half of the suspension is processed directly on a drier as described in example 2 (crystals 4.a), whereas the other half is maintained at 26° C. for 19 hrs (crystals 4.b) before also being treated in the same way.

TABLE 7

| | Lactic acid content % | Quantity of crystals retrieved after washing/drying g |
|---|---|---|
| Crystals 4.a | 99.4 | 320 |
| Crystals 4.b | 99.4 | 93 |

At each step, a portion of the crystals are returned to 90% solution in deionised water before analysis according to the protocols described in examples 1 and 2

The 90% lactic acid solution obtained after washing and suspension of the crystals is also placed in contact with 20 g/l of Norit ROX activated carbon overnight at ambient temperature in a sealed cylinder on an orbital stirrer. The solution is filtered and analysed.

The results of tables 7 and 8 demonstrate the poor quality of the lactic acid crystals produced using the method described in this invention when the starting solution has a lactic acid concentration greater than 95%. This quality is improved by allowing the crystals to mature for 19 hours but the productivity then drops significantly.

The present invention will thus be applied preferentially on starting solutions having a concentration less than or equal to 95%.

TABLE 8

| | Specific surface area by mass $m^2/g$ | Length over thickness ratio L1/L2 | Before crystallisation Colour (fresh solution) (Hazen) | After drying | | After washing (25% of a 90% lactic acid solution, 4° C.) | | After passage on Noritt ROX activated carbon (20 g/l) | | Yield on lactic acid (%) |
|---|---|---|---|---|---|---|---|---|---|---|
| | | | | Colour (fresh solution) (Hazen) | Colour after heating (200° C., 2 hrs) (Hazen)) | Colour (fresh solution) (Hazen) | Colour after heating (200° C., 2 hrs) (Hazen)) | Colour (fresh solution) (Hazen) | Colour after heating (200° C., 2 hrs) (Hazen)) | |
| Crystals 4.a | 0.08 | 9 | 1900 | 350 | 800 | 160 | 400 | 70 | 200 | 34 |
| Crystals 4.b | 0.05 | 3 | 1900 | 150 | 700 | 75 | 90 | 40 | 75 | 10 |

The invention claimed is:

1. Method for purifying lactic acid, in order to obtain crystals having a specific surface area by mass of less than 0.05 $m^2/g$, from an impure aqueous solution having a colour of greater than 500 Hazen at a total acidity concentration between 85 and 95%, characterised in that crystallisation is carried out in a single step, at a temperature not exceeding 30° C., by controlling oligomer content, the oligomer content expressed by monomer content in relation to total lactic acid concentration, in order to maintain the monomer content at a relative content greater than 80%, and by controlling supersaturation of the aqueous lactic acid solution in order maintain the supersaturation between 1 and 60%.

2. The method for purifying lactic acid according to claim 1 characterised in that the oligomer content is controlled by maintaining the monomer content at a relative content greater than 90%.

3. The method for purifying lactic acid according to claim 1 characterised in that:
   (i) The impure aqueous lactic acid solution is cooled at a low degree of supersaturation, between 1 and 40%;
   (ii) The impure aqueous solution is seeded with lactic acid crystals;
   (iii) The crystals are grown at a low degree of supersaturation between 1 and 40%; and
   (iv) The crystals having specific surface area by mass of <0.05 $m^2/g$ are retrieved by separating same from the liquid phase.

4. The method for purifying lactic acid according to claim 3 characterised in that the degree of supersaturation is between 10 and 20%.

5. Method for obtaining heat-stable grade lactic acid crystals, having a specific surface area by mass of less than 0.05 $m^2/g$ wherein a 90% aqueous solution of said crystals has a colour, after heating at 200° C. for 2 hours, of less than 50 Hazen characterised in that an impure aqueous lactic acid solution having a colour of greater than 500 Hazen is purified by crystallisation according to a method described in claim 1.

6. The method for purifying lactic acid according to claim 1 characterised in that the crystals obtained are washed with an aqueous lactic acid solution.

7. The method for purifying lactic acid according to claim 1 characterised in that the impure aqueous solution has a colour of greater than 500 Hazen at a total acidity concentration of between 88 and 93%.

* * * * *